(12) United States Patent
Goessl et al.

(10) Patent No.: US 10,307,509 B2
(45) Date of Patent: *Jun. 4, 2019

(54) HEMOSTATIC FOAM

(71) Applicants: BAXTER INTERNATIONAL INC., Deerfield, IL (US); BAXTER HEALTHCARE S.A., Glattpark (Opfikon) (CH)

(72) Inventors: Andreas Goessl, Vienna (AT); Katarzyna Gorna, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 336 days.

This patent is subject to a terminal disclaimer.

(21) Appl. No.: 14/650,278

(22) PCT Filed: Dec. 6, 2013

(86) PCT No.: PCT/EP2013/075852
§ 371 (c)(1),
(2) Date: Jun. 5, 2015

(87) PCT Pub. No.: WO2014/086996
PCT Pub. Date: Jun. 12, 2014

(65) Prior Publication Data
US 2015/0314037 A1 Nov. 5, 2015

Related U.S. Application Data

(60) Provisional application No. 61/734,544, filed on Dec. 7, 2012.

(51) Int. Cl.
*A61L 26/00* (2006.01)
*A61M 35/00* (2006.01)

(52) U.S. Cl.
CPC ....... *A61L 26/0052* (2013.01); *A61L 26/0028* (2013.01); *A61L 26/0085* (2013.01); *A61M 35/003* (2013.01); *A61L 2400/04* (2013.01)

(58) Field of Classification Search
None
See application file for complete search history.

(56) References Cited

U.S. PATENT DOCUMENTS 4,427,651 A   1/1984 Stroetmann
4,892,826 A   1/1990 Homandberg et al.
(Continued)

FOREIGN PATENT DOCUMENTS

FR   2796558 A1   1/2001
WO   0162312 A1   8/2001
(Continued)

OTHER PUBLICATIONS

Lominadze et al. ('Mechanisms of fibrinogen-induced microvascular dysfunction during cardiovascular disease' Acta Physiol (Oxf.) v198(1) Jan. 2010 pp. 1-13, printed as a total of 20 pages) (Year: 2010).*

(Continued)

*Primary Examiner* — Karlheinz R. Skowronek
*Assistant Examiner* — Ronald T Niebauer
(74) *Attorney, Agent, or Firm* — K&L Gates LLP

(57) ABSTRACT

The invention discloses a pharmaceutical hemostatic liquid foam base preparation comprising albumin as foaming agent and a fibrinogen precipitating substance and optionally a coagulation inducing agent, wherein albumin as foaming agent is present in native form; a method for the production of a transient hemostatic liquid foam; the transient hemostatic liquid foam; and a kit for making the foam.

20 Claims, 6 Drawing Sheets

(56) References Cited

U.S. PATENT DOCUMENTS

| | | | |
|---|---|---|---|
| 6,054,122 | A | 4/2000 | Macphee |
| 6,703,299 | B2 | 5/2004 | Tayot et al. |
| 9,168,325 | B2 * | 10/2015 | Goessl ............... A61L 26/0052 |
| 2003/0211137 | A1 | 11/2003 | Sierra |
| 2007/0254016 | A1 | 11/2007 | Anderson et al. |
| 2010/0249044 | A1 | 9/2010 | Walker |
| 2011/0125089 | A1 | 5/2011 | Senderoff et al. |

FOREIGN PATENT DOCUMENTS

| | | |
|---|---|---|
| WO | 2007/084919 A1 | 7/2007 |
| WO | 2008/065388 A2 | 6/2008 |
| WO | 2009/120432 A2 | 10/2009 |
| WO | 2009/120433 A2 | 10/2009 |
| WO | 2011/151384 A1 | 12/2011 |

OTHER PUBLICATIONS

Wetzel et al. ('Temperature behavior of human serum albumin' Eur. J. Biochem. v104 1980 pp. 469-478) (Year: 1980).*

International Search Report of related PCT/EP2013/075852, dated Feb. 2, 2014, 4 pages.

S. McKee, "Creating Egg White Foams." http:/www.preparedfoods.com/articles/print/112210-creating-egg-white-foams. (accessed Jan. 30, 2015), 3 printed pages, written Jan. 23, 2013.

MA Shuman, PW Majerus. "The Measurement of Thrombin in Clotting Blood by Radioimmunoassay." The Journal of Clinical Investigation, vol. 58, Nov. 1976, pp. 1249-1258.

M. Fasano, S. Curry, E. Terreno, M. Galliano, G. Fanali, P. Narciso, S. Notari, P. Ascenzi. "The Extraordinary Ligand Binding Properties of Human Serum Albumin." International Union of Biochemistry and Molecular Biology Life, vol. 57 (12), Dec. 2005, pp. 787-796.

Federal Register, "2014 Interim Guidance on Patent Subject Matter Eligibility." vol. 79, No. 241, Tuesday, Dec. 16, 2014, pp. 74618-74633.

Office Action dated May 18, 2017 for Japan Patent Application No. 2015-546040; all pages.

Fischer, EG., et al, "Tissue Factor-initiated Thrombin Generation Activates the Sigaling Thrombin Receptor on Malignant Melanoma Cells." Cancer Research, vol. 55, Apr. 15, 1995; pp. 1629-1632.

* cited by examiner

HEMOSTATIC FOAM

CROSS-REFERENCES TO RELATED APPLICATIONS

This application is a 35 U.S.C. § 371 U.S. National Stage Entry of International Application Serial No. PCT/EP2013/075852 (WO 2014/086996) filed Dec. 6, 2013, which claims the benefit of priority to U.S. Provisional Patent Application No. 61/734,544 filed Dec. 7, 2012. This application is also related to U.S. patent application Ser. No. 14/099,712 filed Dec. 6, 2013. The entire content of each of the above filings is incorporated herein by reference for all purposes.

FIELD OF THE INVENTION

The present invention relates to pharmaceutical hemostatic foam formulations.

BACKGROUND OF THE INVENTION

Foams are generally understood to represent materials in which a gas, such as air, is finely dispersed in a liquid in a form that is stable over some time. The liquid is found in the form of thin films between the bubbles. The stabilizing element of such gas dispersions is the surface tension of the liquid phase. The surface tension can be influenced by the presence of surface-active agents in the fluid phase, which help to stabilize the films against collapse. These foams are generally referred to as closed pore foams, as there is no connection between the gas spaces of each individual bubble. If the liquid films are stabilized by other means, e.g. by chemical reactions that transform the liquid phase into a viscoelastic solid, then the formation of open pore foams is possible, in which the fluid bridges are removed in a controlled manner, e.g. by evaporation or other processes. The transformation of the liquid films into a viscoelastic solid material also serves to effectively stabilize the foams against rapid collapse.

It is an object of the present invention to provide improved hemostatic foams which can be safely injected into tissue voids with low visibility and which are effective with no need for approximation. In addition, it is important that such a foam hemostat does not present a risk of obstruction or compression of pressure sensitive organs or tissues due to excessive swelling. Such a foam should be specifically applicable in neuro/spine, laparoscopic and cardiovascular surgery.

SUMMARY OF THE INVENTION

Accordingly, the present invention provides a pharmaceutical hemostatic liquid foam base preparation comprising albumin as foaming agent and a fibrinogen precipitating substance and optionally a coagulation inducing agent, wherein albumin as foaming agent is present in native form.

Another aspect of the present invention is a method for preparing a pharmaceutical hemostatic liquid foam, wherein a pharmaceutical hemostatic liquid foam base preparation according to the present invention is contacted with a foaming gas so as to obtain a pharmaceutical hemostatic liquid foam.

Another aspect of the present invention is a transient pharmaceutical hemostatic liquid foam obtainable by a method according to the present invention, preferably for use as a hemostat, especially for the treatment of wounds.

Another aspect of the present invention is a combination product, preferably a ready-to-use combination product, comprising a pharmaceutical hemostatic liquid foam base preparation according to the present invention and a foaming gas.

Another aspect of the present invention is a kit for producing a transient pharmaceutical hemostatic liquid foam according to the present invention, comprising
(a) a first container comprising a pharmaceutical hemostatic liquid foam base preparation according to the present invention, and
(b) a second container containing a foaming gas.

Another aspect of the present invention is the use of a pharmaceutical preparation according to the present invention for the manufacture of a hemostat, especially a hemostat for the treatment of wounds.

DETAILED DESCRIPTION OF THE INVENTION

Figure 1:
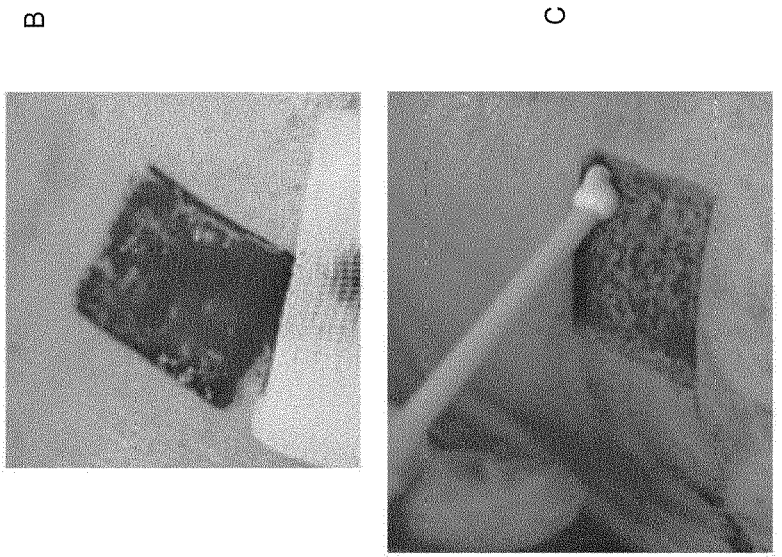
FIG. 1 shows the structure of skin (A), the view of created skin lesion (B) and application of flowable hemostatic foam according to the present invention (C).
Figure 1:
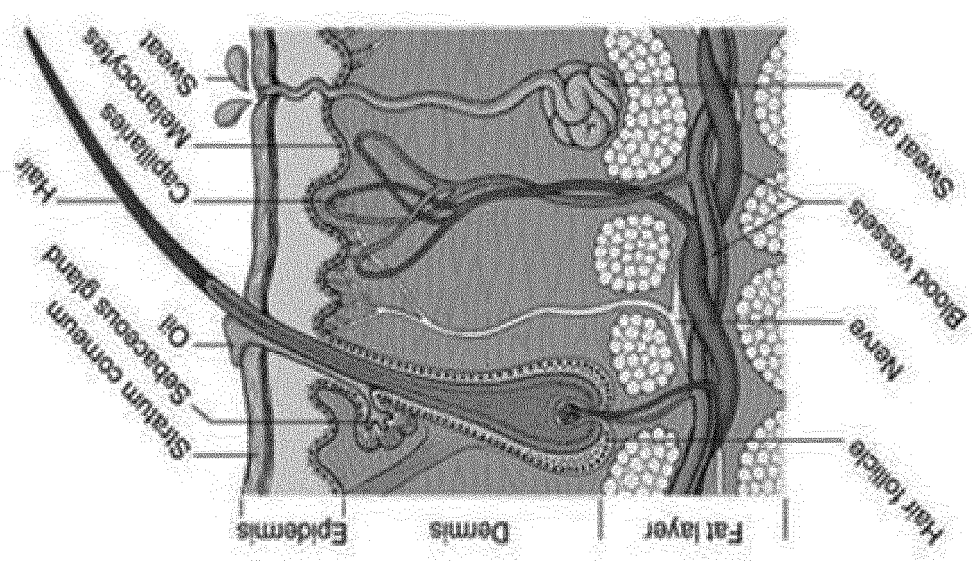

The present invention provides a pharmaceutical hemostatic liquid foam base preparation comprising albumin as foaming agent and a fibrinogen precipitating substance and optionally a coagulation inducing agent, wherein albumin as foaming agent is present in native form. With the foam base according to the present invention, improved hemostatic foams are provided which can be safely injected into tissue voids with low visibility and which are effective with no need for approximation. No excessive swelling or obstruction risks are obtained with the foams according to the present invention. Moreover, the foam according to the present invention is specifically suitable in neuro/spine, laparoscopic and cardiovascular surgery.

It is important for the present invention that albumin is present in the foam base in its native form, i.e. that albumin is properly folded and fully operative and functional. Accordingly, the foam base according to the present invention is essentially free of denatured albumin. "Essentially free" means in this respect that the amount of denatured albumin should be 5% or lower, preferably 2% or lower, especially 1% or lower. Determination of the amount of denatured albumin can easily be performed by methods available to a person skilled in the art, e.g. by native gel electrophoresis or circular dichroism.

"Native form" as used in the present invention includes albumin which has undergone a pre-treatment, such as a pre-treatment by moderate heat or a treatment for removing fatty acids or lipids, such as e.g. filtering over carbon filters.

Preferably, albumin is present in the pharmaceutical preparation as foaming agent from 2 to 40%, preferably from 5 to 25% w/v, more preferably from 10 to 20%, especially about 15%.

Preferably, the albumin used is an albumin which is pharmaceutically acceptable, especially human albumin from human blood plasma or recombinant human protein. For certain uses (where this is appropriate with respect to regulatory guidelines), also animal albumin may be used, e.g. plasmatic or recombinant bovine albumin or albumin (recombinant or plasmatic) from pig, goat, sheep, etc.

Preferred fibrinogen precipitating substances are fibrinogen cleaving substances, preferably selected from the group consisting of thrombin, a snake venom protease or a thrombin precursor. The most preferred fibrinogen cleaving substances is thrombin, which acts in converting fibrinogen to fibrin, which assembles to a sealing, hemostatic fibrin network.

Other preferred fibrinogen precipitating substances are selected from the group consisting of fibrinogen binding peptides, preferably GPRP containing peptides. Examples of such peptides are disclosed in WO 2008/065388 A2. Those peptides may be bound to modified albumin. Such peptide constructs comprising modified albumin can be used as fibrinogen binding substances according to the present invention; however, such modified albumin is not regarded as a foaming agent according to the present invention and would therefore not account to the foaming agent component of the preparation according to the present invention.

The reason for this is that it is specifically preferred that albumin as foaming agent is present in the foam base in a non-crosslinked form. Such albumin foaming agent therefore does neither contain residual amounts of crosslinking agents nor crosslinking moieties (from such crosslinking agent) between the albumin moieties.

Moreover, the foam base should lead to a transient foam to be applied to a wound. It is therefore preferred to omit any kind of chemical stabilizers, such as any reactive substances, e.g. a crosslinking agent. It is specifically preferred to omit the addition of detergents to the pharmaceutical preparation according to the present invention. Accordingly the preparation is preferably essentially free of detergents. "Essentially free" means here a detergent concentration which is 0.5% (v/v) or lower, preferably 0.1% or lower, especially 0.05% or lower.

The preferred fibrinogen precipitating substance according to the present invention is thrombin. Thrombin is preferably present in a concentration of 0.1 IU/ml to 10000 IU/ml, more preferred of 1 IU/ml to 8000 IU/ml, especially 100 to 5000 IU/ml.

It is also preferred to add "active substances", preferably as solutions, but also solids are possible, to the pharmaceutical hemostatic liquid foam base preparation according to the present invention to make the foam preparations even more effective and useful as hemostatic agents. Advantages of presenting such active substances in a foam formulation rather than in solution include the high surface area for enhanced contact between blood and the active substance, and the fact that the active substance is in contact with the bleeding tissue for an extended amount of time compared to a solution, which tends to run off from the wound if not perfectly level.

These active substances can be classified by their mode of action in enhancing the hemostatic activity of the pharmaceutical hemostatic liquid foam base preparation according to the present invention.

Coagulation Factors: These typically are enzymes found in the coagulation cascade and act by enhancing the coagulation cascade of the patient. Examples of coagulation factors, which can be used either alone or in combination are FVII, FVIII, FIX, FX, FXIII, their activated forms, such as e.g. factor VIIa, or FEIBA.

Vitamin K ($K_1$ and $K_3$) can be also considered as coagulant to be added to a foam formulation as it helps to regulate the activity of a number of proteins involved in platelet aggregation, or blood clotting. Vitamin K can help to activate factor X, IX, VII and prothrombin, all proteins that promote blood clot formation.

Platelet activators: Activation of platelets is an essential step in achieving hemostasis, therefore the addition of platelet activators can be a powerful way of enhancing the hemostatic potency of such foam formulations. Collagen is known as a platelet activator, as is thromboxane A2, or arachidonic acid, (the precursor of thromboxane A2), ADP (adenosine diphosphate) and many other substances. In a preferred embodiment collagen is added to the composition of the present invention, especially preferred collagen in solid form is present.

Coagulation inducing substances: are agents that induce blood coagulation (thrombogenesis), i.e. the process by which blood forms clots. Examples of such agents are agents that are naturally inducing coagulation, such as tissue factor, activated platelets, factors IIa (thrombin), Va, VIIa, VIIa, IXa, Xa, XIa, XIIa, XIIIa; or antihemorrhagic agents such as zeolithes, anhydrous aluminium sulfate, potassium alum, titanium dioxide, (microfibrillar) collagen, chitosan, etc.; collagen and ((water) soluble and insoluble) chitosan being specifically preferred coagulation inducing substances. Coagulation inducing substances such as chitosan can be added to further induce coagulation and support the hemostatic characteristics of the preparation according to the present invention. In a preferred embodiment chitosan is present in the composition of the present invention either in solid form or as a solution.

Vasocontrictors: Vasoconstrictors are molecules that lead to a transient narrowing of blood vessel luminal diameter—as such they are useful in hemostasis by temporarily reducing blood flow rate, primarily in the vicinity of the applied foam.

According to another aspect, the present invention relates to a method for preparing a pharmaceutical hemostatic liquid foam, wherein a pharmaceutical hemostatic liquid foam base preparation according to the present invention is contacted with a foaming gas so as to obtain a pharmaceutical hemostatic liquid foam.

Preferably, the foaming gas is selected from the group consisting of air, $N_2$, $O_2$, $N_2O$, $CO_2$, propane, butane, dimethylether, or partly fluorinated hydrocarbons (HFCs), especially 1,1,1,2-Tetrafluoroethane (HFC134a) or 1,1,1,2,3,3,3-Heptafluoropropane (HFC227ea). The foaming gas is preferably used in an amount of 1 to 30% (w/v), especially 5 to 15% (w/v).

The foaming gas may be provided under pressure. For example, the pressurized gas may be introduced into the pharmaceutical hemostatic liquid foam base preparation by a nozzle. It is e.g. possible to introduce the foaming gas directly from a gas cylinder containing the pressurized gas to the foam base.

Accordingly, the foam is preferably created by contacting the pharmaceutical hemostatic liquid foam base preparation with the foaming gas by applying pressure. The pressure may e.g. be implied by a pressurised foaming gas container or by applying physical force by the (hand of the) user of the present foam base, e.g. the surgeon or surgeon assistants.

The mixing of the foaming gas could also be performed under pressure in an appropriate aerosol containing container wherein the foaming gas such as a propellant like R134a, R227ea, DME etc., but not gases such as air, $N_2$, $CO_2$, butane and propane and the like, is in a liquid state and as such solubilised in the liquid formulation of the fibrinogen precipitating substance and/or dispersed therein;

In a preferred embodiment of the method, the pharmaceutical hemostatic liquid foam base preparation is provided in a first container and the foaming gas is provided in a second container. Then the first and the second container are connected so as to allow the pharmaceutical hemostatic liquid foam base preparation to be mixed with the foaming gas to obtain a foam. Preferably, the first and the second container is connected with a mixing device, especially a mixing device selected from the group consisting of a filter material, a porous disc device, a three-dimensional lattice or a matrix material. Preferred examples of such mixing devices (and suitable containers therefor) are disclosed e.g. in WO 2007/084919 A1, WO 2009/120432 A2 or WO 2009/120433 A2.

In a further preferred embodiment mixing can be done in using specific containers or aerosol cans. All components of the formulation are added in solution to a pressure-proof container, which is then closed using a valve assembly of some sort. The propellant gas or liquefied gas (as in the case of R134a) is then added, either through the valve itself or through a secondary port. The propellant either dissolves completely in the liquid formulation, dissolves partially, or the propellant forms a separate phase in the container. In any case, upon dispensing the product through the valve, the gas expands or the liquid gas evaporates from within the liquid formulation, thereby forming a foam upon release.

According to another preferred embodiment of the method, the pharmaceutical hemostatic liquid foam base preparation and the foaming gas is provided in a container and the foam is obtained by mixing the pharmaceutical hemostatic liquid foam base preparation with the foaming gas.

Another aspect of the present invention relates to a combination product, preferably a ready-to-use combination product, comprising a pharmaceutical hemostatic liquid foam base preparation according to the present invention and a foaming gas, preferably a foaming gas selected from the group consisting of air, $N_2$, $O_2$, $N_2O$, $CO_2$, propane, butane, dimethylether, or partly fluorinated hydrocarbons (HFCs), especially 1,1,1,2-Tetrafluoroethane (HFC134a) or 1,1,1,2,3,3,3-Heptafluoropropane (HFC227ea). With such a combination product the foam can easily be produced (e.g. by mixing (especially swooshing) the foam base with the foaming gas in the (common) container of the combination product). This would allow the production of the foam from one container (e.g. a vial or a syringe) immediately at the place of surgery.

According to another aspect, the present invention relates to a transient pharmaceutical hemostatic liquid foam obtainable by a method according to the present invention, preferably for use as a hemostat, especially for the treatment of wounds.

The foam according to the present invention is not stable so that it degrades shortly after administration e.g. to a wound. "Transient" according to the present invention therefore has the meaning that the foam is chemically unstabilized, essentially free of any reactive substances, such as e.g. free of crosslinking agents, and degrades shortly after hemostasis has been achieved, i.e. up to about 5 times the time necessary to achieve hemostasis, e.g. about 10 minutes.

According to another aspect, the present invention relates to a kit for producing a transient pharmaceutical hemostatic liquid foam according to the present invention, the kit comprising (a) a first container comprising a pharmaceutical hemostatic liquid foam base preparation according to the present invention, and (b) a second container containing a foaming gas.

The foaming gas is preferably selected from the group consisting of air, $N_2$, $O_2$, $N_2O$, $CO_2$, propane, butane, dimethylether, or partly fluorinated hydrocarbons (HFCs), especially 1,1,1,2-Tetrafluoroethane (HFC134a) or 1,1,1,2,3,3,3-Heptafluoropropane (HFC227ea).

In a preferred embodiment, the first and the second container are connectable by a mixing device, especially a mixing device selected from the group consisting of a filter material, a porous disc device, a three-dimensional lattice or a matrix material. In a further preferred embodiment it is also possible to produce a composition of the present invention without using a mixing device.

Preferably, the kit is provided in a form, wherein the containers are syringe containers.

Also preferred is the use of aerosol cans for producing a composition of the present invention.

According to another aspect, the present invention relates to the use of a pharmaceutical preparation according to the present invention for the manufacture of a hemostat, especially a hemostat for the treatment of wounds.

The foam base preparation according to the present invention containing human serum albumin (HSA) in an aqueous solution can be expanded in several different directions. Stable, fine-pored foams can be produced using the pharmaceutical hemostatic liquid foam base preparation according to the present invention with a preferred concentration of 5 to 25% albumin (w/v fluid phase). The aqueous solution can be physiological saline (0.9% (w/v), phosphate buffered saline, preferably a solution containing up to 10% (w/v fluid phase) sodium chloride, preferably a solution containing $CaCl_2$ in concentrations up to 40 mM. It is also preferred to use preparations containing sucrose in concentrations of up to 2.5% (w/v fluid phase). In another embodiment it is preferred to use collagen, such as collagen in solid form and/or soluble or insoluble chitosan. A preferred composition of the present invention includes thrombin, albumin and collagen and/or (in)soluble chitosan.

For the example section, foams were created from these preparations e.g. by mixing the solutions in a ratio of typically 1:5 with air (1 ml fluid+4 ml of air). Other fluid to gas ratios are also possible, the limits of the ratio can easily be established for each individual preparation and the intended use and consistency of the foam. Accordingly, ratios ranging from 1:10 to 10:1 (air:fluid) are well within the scope of this invention. Mixing can e.g. be achieved by filling one 5 ml male luer syringe (e.g. B. Braun Injekt) with 1 ml of the respective solution, and another such syringe with 4 ml of air. These two syringes were connected by means for a female-female luer connector. The system was foamed by repeated transfer back and forth of the syringe contents until the entire volume was filled with a fine-pored foam (typically a total of 20 passes). Foaming is improved if the female-female luer contains a porous polypropylene disk according to WO 2007/084919 A1.

Other preferred methods of mixing are:

In-line foam dispenser: Using a gas driven foam set that consisted of a Tisseel Spray head coupled with a female-male luer connector with 2 porous polypropylene disk according to WO 2007/084919 A1 (e.g. FIG. 34). Flowing air through the assembly with 1 bar above atmosphere, and then dispensing the pharmaceutical hemostatic liquid foam base preparation according to the present invention into the air flow and through the 2 mixing disks yielded a stable HSA foam without the need of mechanical mixing.

Introducing the pharmaceutical hemostatic liquid foam base preparation according to the present invention into a pressure-stable vessel, adding $N_2O$ to the solution in the pressure-stable vessel, shaking the solution in the $N_2O$-pressurized vessel, and then releasing the solution to atmospheric pressure through an applicator. In this process, analogous to the formation of whipped cream in the same device and using the same method, a foam was formed. The foam, however, was not as stable as the one created by mechanical mixing with air.

A foam base with thrombin may also be contacted with R134a or propane/butane, which upon release forms a stable transient foam according to the present invention. Coagulation inducing agents such as e.g. collagen and/or (in)soluble chitosan as mentioned above may be added.

Based on the pharmaceutical hemostatic liquid foam base preparation according to the present invention containing HSA in aqueous solutions, formulations containing thrombin in concentrations up to 2500 IU/ml were made and tested in the example section.

The intended use of the pharmaceutical hemostatic liquid foam base preparation according to the present invention is to provide a (transient) hemostatic foam which is e.g. specifically suitable for the treatment of surgical or emergency bleeds on tissue surfaces or in cavities where the application of conventional topical hemostats is difficult or impractical. The foam according to the present invention is intended to achieve hemostasis without the need for approximation of the bleeding site, which make the invention suitable for use in neurological indications where little or no pressure can be applied to the tissues. This also allows the application of the foam according to the present invention in bleeding situations where the exact location of the bleed cannot be determined visually, either because the overall visibility of the surgical field is difficult to achieve (cavities, diffuse bleedings in laparoscopic surgery, etc.) or where achieving hemostasis quickly is critical for the survival of the patient. Hemostasis can be achieved either by mechanically sealing the bleeding surfaces, thus activating the blood clotting cascade inside the capillaries where blood flow is impeded, or by activating blood clotting by chemical, biochemical or physical means, using agents that are delivered within the foam formulations according to the present invention. If the primary mode of action of the foam formulation is by sealing, other sealing indications can also be addressed by these formulations.

The foam formulation according to the present invention can also be seen as a means to achieve extended contact between a bleeding surface and a stand-alone thrombin product frequently used in some geographies as a means to achieve hemostasis.

EXAMPLES

Example 1

1. Summary

Two different hemostats in the form of a "flowable foam" according to the present invention (the pharmaceutical hemostatic liquid foam base preparation according to the present invention) have been tested in non- and heparinized pig in partial thickness skin lesion and in liver abrasion model.

Flowable foams according to the present invention were prepared with two different initial thrombin concentrations of 500 IU/ml and 2500 IU/ml. In both formulations 25% solution of human serum albumin (HSA) was used as a foaming agent.

Hemostatic efficacy of all formulations was initially tested in partial thickness porcine skin lesion, in non-heparinized animal. The lesions with diameter of 2×3 mm and thickness of 1 mm were created using dermatome starting from rump and continued to back. In this type of lesion only diffuse, weak bleeding was achieved. The samples tested were applied 1 min after lesion was created and irrigation of the product was performed 2 min post application. There was no product approximation.

All formulations tested showed satisfactory hemostatic efficacy in the porcine skin model. An overall perception was that the formulation with higher concentration of thrombin (2500 IU/ml) was slightly better that formulation with lower Thrombin concentration.

In the second model—swine liver abrasion model when the pig was still not heparinized there was no perceptible differences in hemostatic performance of the products.

At the end of in vivo test, the formulation with higher thrombin concentration was tested in liver abrasion model in heparinized pig and at this condition the samples could not stop bleeding.

In the case of strong bleeding in heparinized animal flowable foam hemostats require further optimization as under such conditions proposed formulations were not effective.

2. Scope of the Experiments

A hemostatic, adherent foam formulation that is biocompatible and fully bio-resorbable is provided with the present invention as one of an appealing option for new generation product in hemostasis.

The foam should safely be injected into tissue voids with low visibility and should be effective with no need for approximation. Additional important requirement of the foam hemostat is absence of excessive swelling or obstruction risk. Main application of such flowable hemostatic foam involves neuro/spine, laparoscopic and cardiovascular surgery.

Flowable foam systems according to the present invention based on human serum albumin mixed with thrombin have been designed. It has been found that concentrated solution of HSA when mixed 1:3 with air, results with stable over longer time (10 min) foam that can be prepared using two syringes connected with special mixing unit. Such foam can be further applied through the same application tip that is used in Floseal Hemostatic Matrix.

The purpose of these experiments was to test hemostatic efficacy of selected flowable foam formulations according to the present invention. The formulations were tested at moderate bleeding in two different models in non-heparinized pig. In the first model the formulations were tested in partial thickness skin lesion and in the second model in liver abrasion lesion. Efficacy of the samples were assessed only qualitatively.

3. Materials 3.1 Used Raw Materials

| Material | Supplier | Lot Number |
|---|---|---|
| Thrombin SD TIM5 500 IU/ml US 5 ml | Baxter | VNF4K001A |

3.2 Solutions
HSA 25%
Calcium-chloride sol. 40 mM 5 ml
Thrombin sol. 500 IU/ml in CaCl$_2$ 40 mM
Thrombin solution 2500 IU/ml in CaCl$_2$ 40 mM
Sodium-chloride solution 0.9%
3.3 Equipment/Disposables

| Equipment/disposables | Supplier |
|---|---|
| Syringes 5 ml Luer-Lock solo | BBraun |
| Rapid-fill-connector, Luer-lock-to-luer-lock | Baxa |
| Mixing device "Mix-F" | Baxter |
| FloSeal applicators Tip Large 6.35 mm | Baxter |
| Abrasion device, d = 18 mm | Dremel |
| Timer | Huger |

Figure 2:
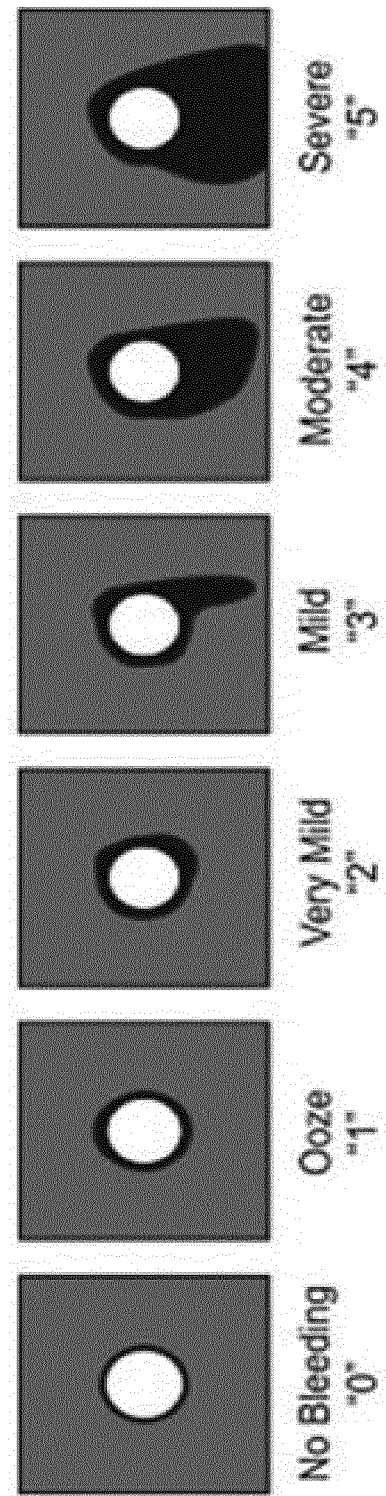
FIG. 2 shows the degree of Bleeding Scale Scores (Bleeding score:
  0 no bleeding—product saturated with blood
  1 ooze—blood out of product but no blood drop
  2 very mild—blood drop on the product
  3 mild—blood drop streams down
  4 moderate—small amount of blood streams down
  5 severe—large amount of blood streams down.

4. Methods 4.1 Sample Preparation
4.1.1 Thrombin 500 IU/ml+HSA 25%+4 ml Air
Thrombin 500 IU/ml in CaCl$_2$ 40 mM+4 ml Air:

Thrombin 500 IU/ml lyo vial was dissolved in 5 ml calcium-chloride solution 40 mM. 0.5 ml of the Thrombin solution and 4 ml air were drawn up in 5 ml syringes each. The syringes were then closed with caps and stored at −20° C. until further use.
HSA 25%:

0.5 ml of human albumin serum 25% was drawn up in 5 ml syringes each. The syringes were closed with caps and stored at +4° C. until further use.
4.1.2 Thrombin 2500 IU/ml+HSA 25%+4 ml Air
Thrombin 2500 IU/ml in CaCl$_2$ 40 mM+4 ml Air:

Thrombin 500 IU/ml lyo vials were dissolved in 1 ml calcium-chloride solution 40 mM each. 0.5 ml of the Thrombin solution and 4 ml air were drawn up in 5 ml syringes each. The syringes were then closed with caps and stored at −20° C. until further use.
HSA 25%:

0.5 ml of human albumin serum 25% was drawn up in 5 ml syringes each. The syringes were closed with caps and stored at +4° C. until further use.
4.2 Sample Reconstitution
4.2.1 Thrombin 500 IU/ml+HSA 25%:
0.5 ml Thrombin 500 IU/ml in CaCl$_2$ 40 mM
+
0.5 ml HSA 25%
↓+"Mix-F"
Swooshing 10× (20 passes)
↓
Application with applicator tip 6.35 cm
4.2.2 Thrombin 2500 IU/ml+HSA 25%:
0.5 ml Thrombin 2500 IU/ml in CaCl$_2$ 40 mM
+
0.5 ml HSA 25%
↓+"Mix-F"
Swooshing 10× (20 passes)
↓
Application with applicator tip 6.35 cm
4.3 Surgical Procedure and Bleeding Assessment Initially, all foam formulations were tested in porcine skin lesion and liver abrasion model in non-heparinized animal. Only one sample from formulation with higher thrombin concentration (2500 UI/ml) was tested in liver abrasion model in heparinized pig.
4.3.1 1 mm Partial Thickness Porcine Skin Lesion The lesions with diameter of about 2×3 mm and thickness of 1 mm were created using dermatome starting from rump and continued to back of non-heparinized pig. After lesion was created, exact size of the skin defect was measured. A product was applied 1 min after lesion was created. Before application the excess of blood from the lesion was swabbed (blotted) with gauze and the product was homogenously distributed on the lesion as illustrated in FIGS. 1 (B) and (C). In this type of lesion only diffuse, weak bleeding was achieved. The samples tested were applied without approximation. Irrigation of the product was performed 2 and 5 min post application.
4.3.2 Swine Liver Abrasion Model In this model, liver abrasions were created using a hand-drill dremel fixed with medium grade sandpaper. The refined model reduces variability by using standardized 1.8 cm diameter, about 1 mm deep lesions. With a flat, round, rotating abrasion tool a circular bleeding wound (1.8 cm diameter) was created on the liver lobe surface of a pig. Before application the excess of blood from the lesion was swabbed (blotted) with gauze and next product was homogenously distributed on the lesion. There was no product approximation. The hemostatic efficacy was evaluated after 2, 3, 5 and 10 minutes. Excess of product was irrigated with Ringer solution at 5 min post application.
4.3.3 Bleeding Assessment Bleeding from the crated lesion in both models (skin and liver) was assessed qualitatively (subjectively) according to the scale presented in FIG. 2. Product was prepared and applied onto created lesion. There was no approximation after product has been applied. Excess of product was irrigated with Ringer solution in 20 ml syringe. The degree of bleeding was assessed after 30 sec, and then approximately after 1, 2, 5 and 10 min. Product saturated with blood but without active bleeding were scored as 0. The same saline solution was used to irrigate excess product from the lesion after the 5 minute since application.
Bleeding Score:

| 0 | no bleeding | product saturated with blood |
| 1 | ooze | blood out of product but no blood drop |
| 2 | very mild | blood drop on the product |
| 3 | mild | blood drop streams down |
| 4 | moderate | small amount of blood streams down |
| 5 | severe | large amount of blood streams down |

5. Results

Each tested product was in the form of (transient) flowable foam according to the present invention.

5.1 Thrombin 500 IU/ml+HSA 25%; Porcine Skin Model

Figure 3:
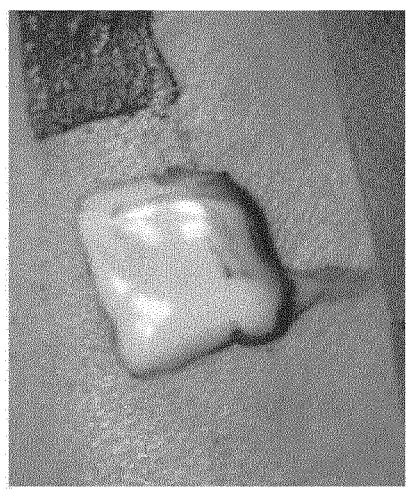
FIG. 3 shows the product according to the present invention with thrombin 500 IU/ml+HSA 25% applied at 0 (A), 2 min (B), after irrigation (C) and at 5 min post application (D) in the porcine skin model.
Figure 3:
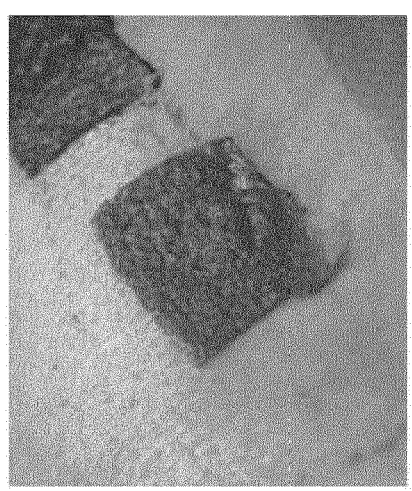
Figure 3:
Figure 3:

The results are depicted in FIG. 3. The foam was prepared and applied to a bleeding lesion. With time liquid oozing was observed most probably due to gravitation of liquid (drainage of liquid to the foam base). Excess of the product could be irrigated away with Ringer solution. The product was tested in three applications with final score "0"—hemostatic success.

5.2. Thrombin 2500 IU/ml+HSA 25%; Porcine Skin Model

Figure 4:
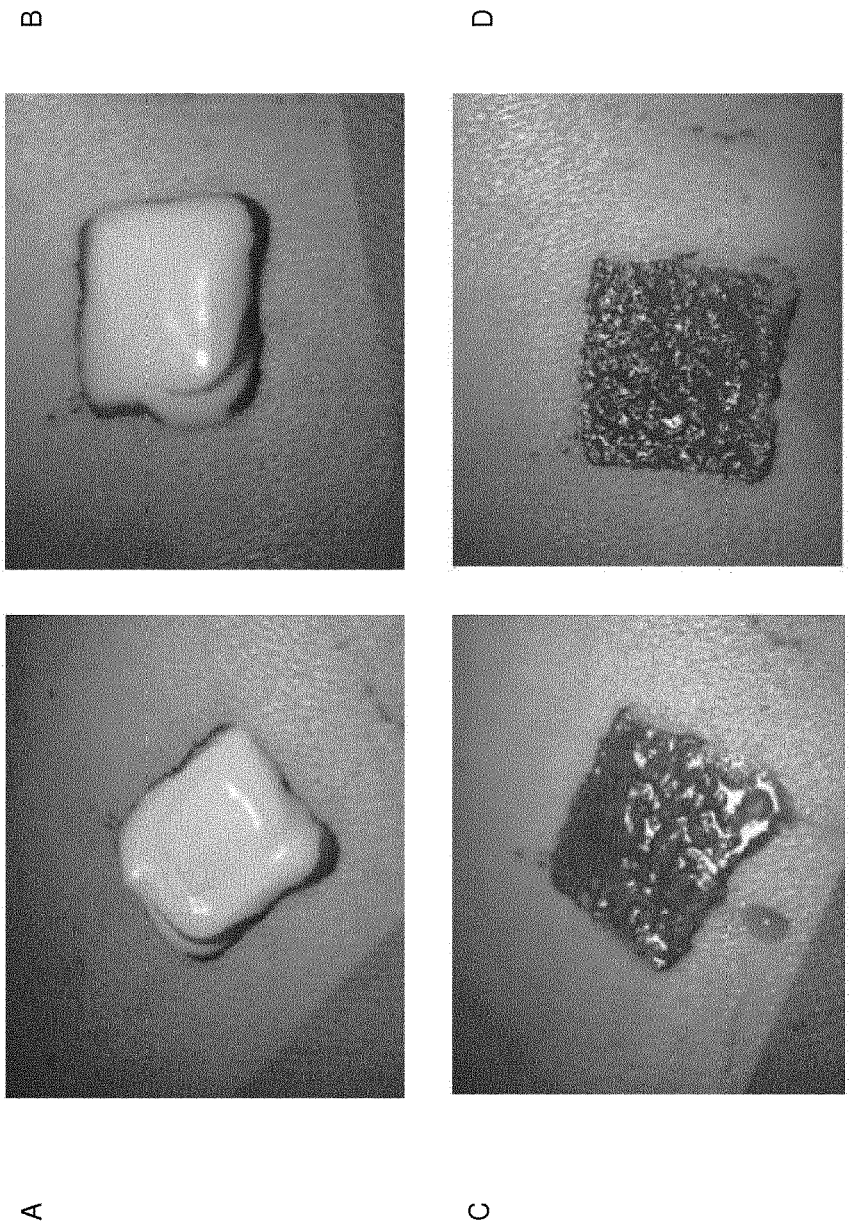
FIG. 4 shows the product according to the present invention with thrombin 2500 IU/ml+HSA 25% applied at 0 (A), 2 min (B), after irrigation (C) and at 5 min post application (D) in the porcine skin model.

The results are depicted in FIG. 4. The foam was prepared and applied to a bleeding lesion. Excess of the product could be irrigated away with Ringer solution. The product was tested in three applications with final score "0"—hemostatic success.

5.3 Thrombin 500 IU/ml+HSA 25%; Liver Abrasion Model

Figure 5:
FIG. 5 shows the product according to the present invention with thrombin 500 IU/ml+HSA 25% applied at 0 (A), 2 min (B), after irrigation (C) and at 10 min post application (D) in the liver abrasion model.
Figure 5:
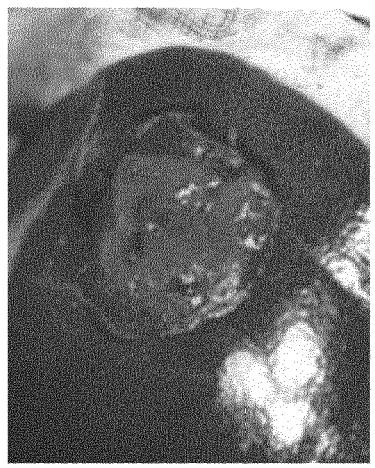
Figure 5:
Figure 5:
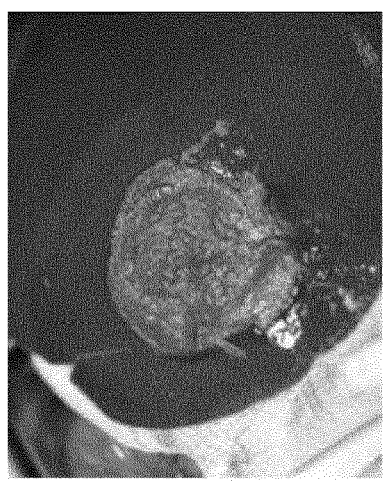

The results are depicted in FIG. 5. Two samples were tested with final score "0"—hemostatic success.

5.4 Thrombin 2500 IU/ml+HSA 25%; Liver Abrasion Model

Figure 6:
FIG. 6 shows the product according to the present invention with thrombin 2500 IU/ml+HSA 25% applied at 0 (A), 2 min (B), after irrigation (C) and at 10 min post application (D) in the liver abrasion model.
Figure 6:
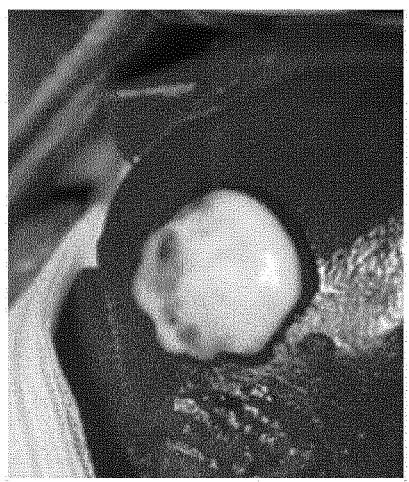
Figure 6:
Figure 6:
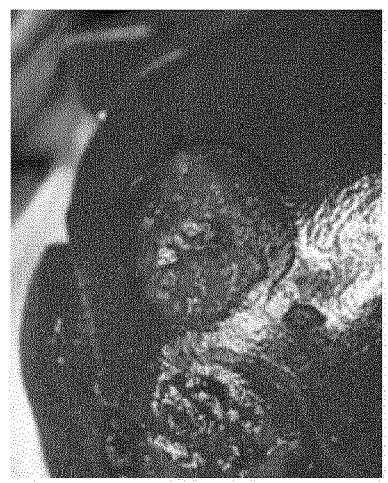

The results are depicted in FIG. 6. Two samples were tested with final score "0"—hemostatic success.

6. Discussion

In order to obtain the liquid foam according to the present invention was mixed 1:3 with air using two syringes connected with special mixing unit. Such foams were observed to be stable over 10 min and could be further applied through an application tip the same as it is used in Floseal Hemostatic Matrix.

The purpose of these experiments was to test hemostatic efficacy of these foam formulations. The formulations were tested at moderate bleeding in two different models in non-heparinized pig. In the first model the formulations were tested in partial thickness skin lesion and in the second model in liver abrasion lesion. Efficacy of the samples was assessed only qualitatively.

Flowable foams according to the present invention were prepared with two different initial thrombin concentrations of 500 IU/ml and 2500 IU/ml. In both formulations 25% solution of HSA was used as a foaming agent.

Hemostatic efficacy of all formulations was initially tested in partial thickness porcine skin lesion, in non-heparinized animal. The lesions with diameter of 2×3 mm and thickness of 1 mm were created using dermatome starting from rump and continued to back. In this type of lesion only diffuse, weak bleeding was achieved. The samples tested were applied 1 min after the lesion was created and irrigation of the product was performed 2 min post application. There was no product approximation.

All formulations tested showed satisfactory hemostatic efficacy in the porcine skin model. An overall perception was that the formulation with higher concentration of thrombin (2500 IU/ml) was slightly better that formulation with lower thrombin concentration.

In the second model—swine liver abrasion model when the pig was still not heparinized there was no perceptible differences in hemostatic performance of the products.

Example 2

A Hemostatic Foam based on human serum albumin (HSA), thrombin and air was prepared by mixing one part of 25% HSA solution with one part of a thrombin solution containing 500 IU/ml thrombin and 5% HSA in a syringe with at least 5 ml volume. The third component was air at 80 vol %; the air was in a second syringe of the same size. The foam was prepared by rapidly transferring the contents of both syringes back and forth at least 20 times through a connector fitted with a sintered porous polypropylene disk (called "Mix F"). This produced a stable, white transient foam with excellent hemostatic properties.

Example 3

A foam prepared as in example 2 was applied to a liver abrasion wound of a pig heparinized to 1.5-2×ACT, which presents mild to moderate bleeds. No breakthrough bleeding was observed in the first 5 minutes after application. After 5 minutes, the remaining foam was irrigated with sterile saline. A stable foam blood clot had formed that presented a mechanically stable, yet compliant and thin wound cover.

Example 4

Further foam stabilization over the formulation presented in example 2 can be achieved as follows: HSA 25%-thrombin (5% HSA, 500 IU/ml) 1:1 mixture containing additionally with 5% (w/v) of polyvinylpyrolidone (PVP). 0.5 g of PVP were dissolved in 10 ml mixture of 25% HSA and thrombin 500 IU/ml. From this solution 1 ml was drawn into a 5 ml syringe and mixed with 4 ml of air in a second 5 ml syringe by rapidly transferring the contents of both syringes back and forth at least 20 times through a connector fitted with a sintered porous polypropylene disk (called "Mix F"). The final formulation contains: 12.5% HSA, 250 IU/ml thrombin and 5% PVP.

Example 5

When placing the foams produced according to example 2 and 4 onto a petri dish which contained 5 ml of human plasma and monitoring the diameter of the foam over the time course of 20 minutes (foam stability assay), a significantly slower spreading of the foam produced according to example 3 was observed, hence the foam was more stable.

Example 6

Chitosan 0.5% foam: From a 1% solution of chitosan, 0.5 ml were added to 1 ml of the 25% HSA and thrombin solution of example 2. The solution in 5 ml syringe was mixed with 4 ml of air in the second 5 ml syringe through Mix F connector to produce a stable foam. When subjected to the foam stability test as described in example 5, and significantly slower spreading of the foam produced according to example 6 was observed, hence the foam was more stable.

Example 7

Chitosan 0.5% foam in aerosol spray can: From a 1% solution of chitosan, 0.5 ml was added to 1 ml of the 25% HSA and thrombin solution of example 2. 10 ml of this solution were filled in a 50 ml aerosol can, and a valve assembly was fitted. 2 g of R134a were filled into the aerosol can through the valve assembly. Upon dispensing of the liquid, a stable foam was formed with the same characteristics as the foam produced manually in syringes.

Example 8

A aerosol spray can according to example 7 was used to dispense a thrombin containing liquid foam onto an abrasion lesion of the pleura in a porcine animal model. The foam was easy to place on the vertical pleural wall, and remained in place until hemostasis was achieved. If necessary, the product can be reapplied to extend the contact time.

Example 9

Foam formulation with solid collagen powder: 34 mg crosslinked collagen were mixed with 1 ml 25% HSA and 1 ml of thrombin 1500 IU/ml solution. To this suspension 150 µl of 1% chitosan solution were added and mixed by rapidly transferring the contents of both syringes back and forth at least 20 times between two 10 ml B. Braun syringes. The amount of the air was set to 4 ml. The foam was produced again by the same process of rapidly transferring the contents of both syringes back and forth at least 20 times. A stable, white transient foam was produced that showed better efficacy in the porcine animal model described in example 3.

Example 10

Collagen (100 mg) foam: 1.5 ml 25 wt % HSA was mixed by swooshing with 100 mg of milled collagen paste and 1 ml of air. The amount of air in the foam was incrementally (each time 1 ml) increased up to total amount of 3 ml in order to obtain foam like structure. Preparation of this formulation was done using 10 ml syringes.

The invention claimed is:

1. A combination product comprising:
  a pharmaceutical hemostatic liquid foam base preparation, wherein the pharmaceutical liquid foam base preparation comprises albumin as foaming agent and a fibrinogen precipitating substance, wherein the albumin as foaming agent is present in native form, and
  a foaming gas, wherein:
    the pharmaceutical hemostatic liquid foam base preparation is a solution and
    the concentration of the albumin in the pharmaceutical hemostatic liquid foam base preparation is from 5% to 40% w/v.

2. A pharmaceutical hemostatic liquid foam obtainable by a method comprising:
  providing a pharmaceutical hemostatic liquid foam base preparation comprising albumin and thrombin, wherein:
    albumin is present in its native form,
    albumin is not crosslinked, and
    thrombin is present in a concentration of 100 to 10000 IU/ml; and
  contacting the pharmaceutical hemostatic liquid foam base preparation with a foaming gas so as to obtain the pharmaceutical hemostatic liquid foam, wherein:
    the pharmaceutical hemostatic liquid foam base preparation is a solution,
    the pharmaceutical hemostatic liquid foam degrades in less than or equal to about 5 times the time necessary to achieve hemostasis, and
    the concentration of the albumin in the pharmaceutical hemostatic liquid foam base preparation is from 5% to 40% w/v.

3. A kit for producing a pharmaceutical hemostatic liquid foam, comprising
  (a) a first container comprising a pharmaceutical hemostatic liquid foam base preparation, wherein the pharmaceutical hemostatic liquid foam base preparation comprises:
    albumin in its native form, and
    a fibrinogen precipitating substance, and
  (b) a second container containing a foaming gas, wherein:
    the pharmaceutical hemostatic liquid foam base preparation is a solution and
    the concentration of the albumin in the pharmaceutical hemostatic liquid foam base preparation is from 5% to 40% w/v.

4. The kit according to claim 3, wherein the foaming gas is selected from the group consisting of air, $N_2$, $O_2$, $N_2O$, $CO_2$, propane, butane, dimethylether, or partly fluorinated hydrocarbons (HFCs).

5. The kit according to claim 3, wherein the first and the second container are connectable by a mixing device.

6. The kit according to claim 3, wherein the containers are syringe containers.

7. The kit according to claim 3, wherein the concentration of the albumin in the pharmaceutical hemostatic liquid foam base preparation is from 10% to 20% w/v.

8. The kit according to claim 3, wherein the concentration of the albumin in the pharmaceutical hemostatic liquid foam base preparation is about 15% w/v.

9. The kit according to claim 3, wherein the pharmaceutical hemostatic liquid foam base preparation is essentially free of detergents.

10. The kit according to claim 3, wherein the pharmaceutical hemostatic liquid foam base preparation further comprises a coagulation inducing agent.

11. The kit according to claim 3, wherein:
  the pharmaceutical liquid foam base preparation further comprises denatured albumin, and
  5% or lower of the combined albumin in its native form and denatured albumin in the pharmaceutical hemostatic liquid foam base preparation is denatured albumin.

12. The kit according to claim 3, wherein:
  the pharmaceutical liquid foam base preparation further comprises denatured albumin, and
  2% or lower of the combined albumin in its native form and denatured albumin in the pharmaceutical hemostatic liquid foam base preparation is denatured.

13. The kit according to claim 3, wherein:
  the pharmaceutical liquid foam base preparation further comprises denatured albumin, and
  1% or lower of the combined albumin in its native form and denatured albumin in the pharmaceutical hemostatic liquid foam base preparation is denatured.

14. The kit according to claim 3, wherein the pharmaceutical hemostatic liquid foam base preparation is free of a crosslinking agent.

15. The combination product according to claim 1, wherein the foaming gas is selected from the group consisting of consisting of air, $N_2$, $O_2$, $N_2O$, $CO_2$, or partly fluorinated hydrocarbons (HFCs).

16. The pharmaceutical hemostatic liquid foam according to claim 2, wherein the pharmaceutical hemostatic liquid foam is stable for less than or equal to 10 minutes.

17. The kit according to claim 3, wherein the pharmaceutical hemostatic liquid foam base preparation consists of albumin in its native form, the fibrinogen precipitating substance, saline, and at least one of a coagulation factor, a platelet activator, a coagulation inducing substance, or a vasoconstrictor.

18. The pharmaceutical hemostatic liquid foam according to claim 2, wherein the pharmaceutical hemostatic liquid foam consists of the foaming gas and the pharmaceutical hemostatic foam base preparation.

19. The kit according to claim 3, wherein the contents of the second container consist of air.

20. The kit according to claim 3, further comprising a mixing device wherein the first and second containers are connectable by the mixing device.

* * * * *